(12) United States Patent
Koller (10) Patent No.: US 6,468,750 B1
(45) Date of Patent: Oct. 22, 2002

(54) CELL REGULATION FACTOR TTO 20

(75) Inventor: Klaus-Peter Koller, Bad Soden (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/561,989

(22) Filed: May 2, 2000

(30) Foreign Application Priority Data

May 3, 1999 (DE) .......................................... 199 20 004

(51) Int. Cl.[7] .......................... C12Q 1/68; C12P 21/06; C12N 1/00; C12N 15/00; C12N 1/20; C07K 17/00; C07H 21/04

(52) U.S. Cl. ........................ 435/6; 435/69.1; 435/252.3; 435/252.33; 435/320.1; 435/810; 530/350; 536/23.1; 536/23.5

(58) Field of Search .................... 530/350; 536/23.5, 536/23.1; 435/69.1, 252.3, 810, 252.33, 320.1, 6

(56) References Cited

U.S. PATENT DOCUMENTS 5,643,758 A * 7/1997 Guan et al.
6,200,802 B1 * 3/2001 Greene et al.

FOREIGN PATENT DOCUMENTS

EP 0 705 842 A 4/1996

OTHER PUBLICATIONS

Ngo et al., in The Protein Folding Problem and Tertiary Structure Prediction, 1994, Merz, et al., (ed.), Birkhauser, Boston , MA, pp. 433 and 492–495.*
Skolnick et al., From genes to protein structure and function: novel applications of computational approaches in the genomic era, Jan. 2000, Trends in Biotech. 18(1):34–39.*
Voet et al., Biochemistry I, 1990, pp. 126–234.*
Attwood et al., The babel of bioinformatics, Oct. 2000, Science 290 (5491): 471–473.*
T. Nagase et al., "Human mRNA for KIAA0282 gene", Database EMBL Sequences 'Online! Accession No. D87458, Nov. 9, 1996; XP002145648.

* cited by examiner

*Primary Examiner*—Christina Chan
*Assistant Examiner*—Phoung N. Huynh
(74) *Attorney, Agent, or Firm*—Finnegan, Henderson, Farabow, Garrett & Dunner, L.L.P.

(57) ABSTRACT

The invention relates to the cell regulation factor TTO 20, DNA coding therefor, its preparation and use, antibodies binding to TTO 20 and the use of DNA coding for TTO 20 and an antibody binding to TTO 20 for use in a diagnostic kit for the detection of inflammatory disorders, in particular rheumatoid arthritis.

9 Claims, 4 Drawing Sheets

SEQUENCE LISTING

<160> NUMBER OF SEQ ID NOS: 10

<210> SEQ ID NO 1
<211> LENGTH: 16
<212> TYPE: DNA
<213> ORGANISM: Homo sapiens

<400> SEQUENCE: 1
caactcctgt atcacc                                                    16

<210> SEQ ID NO 2
<211> LENGTH: 19
<212> TYPE: DNA
<213> ORGANISM: Homo sapiens

<400> SEQUENCE: 2
agtgcgatgt cttctactg                                                 19

<210> SEQ ID NO 3
<211> LENGTH: 20
<212> TYPE: DNA
<213> ORGANISM: Homo sapiens

<400> SEQUENCE: 3
tctaaaggca ggagaggaac                                                20

<210> SEQ ID NO 4
<211> LENGTH: 20

```
<212> TYPE: DNA
<213> ORGANISM: Homo sapiens

<400> SEQUENCE: 4
ttcatgtgtc ttgcttactc                                              20

<210> SEQ ID NO 5
<211> LENGTH: 45
<212> TYPE: DNA
<213> ORGANISM: Homo sapiens

<400> SEQUENCE: 5
ataagaatgc ggccgctaaa ctatcaggaa gatgctttca agttc                  45

<210> SEQ ID NO 6
<211> LENGTH: 19
<212> TYPE: DNA
<213> ORGANISM: Homo sapiens

<400> SEQUENCE: 6
acaggctctc cttttgcac                                               19

<210> SEQ ID NO 7
<211> LENGTH: 27
<212> TYPE: DNA
<213> ORGANISM: Homo sapiens

<400> SEQUENCE: 7
ggaattcgat cagatctctc actgcac                                      27

<210> SEQ ID NO 8
<211> LENGTH: 27
<212> TYPE: DNA
<213> ORGANISM: Homo sapiens

<400> SEQUENCE: 8
ggaattcact tctgtgcagt aacagag                                      27

<210> SEQ ID NO 9
<211> LENGTH: 3262
<212> TYPE: DNA
<213> ORGANISM: Homo sapiens

<400> SEQUENCE: 9
gccctggccc cggtgccccg caactcctgt atcacctgcc cccagtgtca ccgcagcctc   60
atcctggatg accgggggct ccgcggcttc cccaagaatc gcgtactgga agggtaatt   120 gaccgctacc agcagagcaa agccgcggcc ctcagtgcc agctctgcga gaaggcgccc   180
aaggaagcca ccgtcatgtg cgaacagtgc gatgtcttct actgcgatcc gtgccgcctg   240
cgctgccacc cgccccgggg gccctagcc aagcaccgcc tggtgcccc ggcccagggt   300 cgtgtgagcc ggaggctgag cccacgcaag gtctccacct gcacagacca cgagctggag   360
aaccacagca tgtactgcgt gcaatgcaag atgcccgtgt gctaccagtg cttggaggag   420 ggcaaaacact ccagccacga agtcaaggct ctggggcca tgtggaaact acataagagc   480
cagctctccc aggcgctgaa cggactgtca gacaggggca agaagccaa ggagtttctg   540 gtacagctgc gcaacatggt ccagcagatc caggagaaca gtgtggagtt tgaagcctgt   600
ctggtggccc aatgtgatgc cctcatcgat gccctcaaca aagaaaagc ccagctgctg   660 gcccgcgtca caaggagca tgagcacaag ctgaaggtgg ttcgagatca gatctctcac   720
```

```
tgcacagtga aattgcgcca gaccacaggt ctcatggagt actgcttgga ggtgattaag     780
gaaaatgatc ctagtggttt tttgcagatt tctgacgccc tcataagaag agtgcacctg     840
actgaggatc agtggggtaa aggcacactc actccaagga tgaccacgga ctttgacttg     900
agtctggaca cagccctct gctgcaatcc atccaccagc tggatttcgt gcaagtgaaa      960
gcttcctctc cagtcccagc aacccctatc ctacagctgg aggaatgttg tacccacaac    1020
aacagcgcta cgttgtcctg gaaacagcca cctctgtcca cggtgcccgc cgatggatac    1080
attctggagc tggatgatgg caacggtggt caattccggg aggtgtatgt ggggaaggag    1140
acaatgtgca ctgtggatgg tcttcacttc aacagcacat acaacgctcg ggtcaaggcc    1200
ttcaacaaaa caggagtcag cccgtacagc aagaccctgg tcctccaaac gtctgagggt    1260
aaggcccttc agcagtatcc ctcagagcga gaactgcgtg gcatctaaag tggctggcaa    1320
gcccggaggt aaccccacca ctgcccacat tcctgaagtg tttccatgac ttgctctgca    1380
ttctgcacag agccgctgtt cctctcctgc ctttagagag cctatggtat gtggatgtga    1440
tcaaaccaaa gattccacat cggcagttcc aatggcttgg gccggcggct cctttgata     1500 acaatctaaa taagctgcag ttgaagaagc tgaaaaatga aggcctgaat gtgcccctgg    1560
tgtgtaagac aaatgtatct aggctctaga gcaggctccc attctccacc gatacacatc    1620
atgtgccagt tttgcccaga tgattctaaa ttactctgta gtacttgctt gttctgaggg    1680
tgggacctag gttctttcca gtcgtggatt tgtatgactg aatgtgtttc aaatgggtgg    1740
tggggtgcta gagctgttta gagagggcct gttggctgct cctggcttac ccacttagac    1800
tgcctccgtt tcatacccaa agcggaggcc gtcagcacca ggattgagac ttcctgtggg    1860
caccaaacag gaagagacca gcaacttcgc attacccgcc attttcatct tgccagtcc     1920 cttcagtctt ggctaggcta ccgagagcca ccatacaagg ttcatctcta gagaattttt    1980
gcttcttagc tatactttaa atattttggt catcaaagac aagtaatgtg tctcagatga    2040
gaggcttgaa tttgatggcc agatataacc tctgaggctt taacatttt catttttaaga    2100 gtaagcaaga cacatgaaat taaacctaca aggaggtatt gtggctggt gccaaagcat     2160 tctgacactt tggggtgtca ttttaatcaa agaaatcacc cccccacctc accgggattc    2220
tccataactt ccctctgcag aactaattat gttgattttg ttcaagttca agatgttagc    2280
taaaagaact atggtggtgt ttttttttccc acttcccaca aacctcaaca tgtgccagtc    2340
accctaaaat gcttcacatg gttaaaaaca agcacaattt tgaatcctac agcaaggatg    2400
aaaggcccct agccgtgaaa acagtgcttt ggggagcagt tgtcagtcta agtgatgcta    2460
ttccaagaga aggatatgct gagggaaaat gcccacatga cctgttccca tttggagtac    2520
agtgatgtgg tagctacagc ttcccccaga attatcattt tagcaccttc tctcagggat    2580
gacctatcag tttgagagca gttgcctctt ttctcaaaat accatactaa ctgctaaagc    2640
cctccaagag tctttcctag atgcaacgca gaaggcccctt gctggtgatg gcctcatttc    2700
ccatgtgtgt acaaggtggt ttgattgaag agtgaagtgc atgcctgcag agcagagaga    2760
aatttgtagc aatgttgcta atatgtgtta tcagatctgc gggaaaacta tttctattca    2820
taatacatca tgggaatcat actattctgg taaaaatcag ttattagcat aacagcctga    2880
gcacttatgt ctctcgtttc atcctgcagg aggatgtagc gcctcagttt attttaatgt    2940
tcataagatt atggtgtcta atttaataaa ttacaggatt ggaactgcga tccttggtac    3000
cacagtcaca gaactggggg tcattttcta gatgaaacaa acggaacaag ttctcttcca    3060
acaaagaaac tgtactgtag aaattaattt cctccatgaa ttttatatat tgtgtacaaa    3120
```

```
tataaggtat gtatctgaat acaaagaaaa gcctatcatc atatagatat cagtattctc      3180
tgttactgca cagaagtaat tttctcatga tgaaataaag ttcacacaca tactttctcc      3240
ataaaaaaaa aaaaaaaaaa aa                                               3262
```

<210> SEQ ID NO 10
<211> LENGTH: 435
<212> TYPE: PRT
<213> ORGANISM: Homo sapiens

<400> SEQUENCE: 10

```
Ala Leu Ala Pro Val Pro Arg Asn Ser Cys Ile Thr Cys Pro Gln Cys
 1               5                  10                  15

His Arg Ser Leu Ile Leu Asp Asp Arg Gly Leu Arg Gly Phe Pro Lys
            20                  25                  30

Asn Arg Val Leu Glu Gly Val Ile Asp Arg Tyr Gln Gln Ser Lys Ala
        35                  40                  45

Ala Ala Leu Lys Cys Gln Leu Cys Glu Lys Ala Pro Lys Glu Ala Thr
    50                  55                  60

Val Met Cys Glu Gln Cys Asp Val Phe Tyr Cys Asp Pro Cys Arg Leu
65                  70                  75                  80

Arg Cys His Pro Pro Arg Gly Pro Leu Ala Lys His Arg Leu Val Pro
                85                  90                  95

Pro Ala Gln Gly Arg Val Ser Arg Leu Ser Pro Arg Lys Val Ser
            100                 105                 110

Thr Cys Thr Asp His Glu Leu Glu Asn His Ser Met Tyr Cys Val Gln
            115                 120                 125

Cys Lys Met Pro Val Cys Tyr Gln Cys Leu Glu Glu Gly Lys His Ser
    130                 135                 140

Ser His Glu Val Lys Ala Leu Gly Ala Met Trp Lys Leu His Lys Ser
145                 150                 155                 160

Gln Leu Ser Gln Ala Leu Asn Gly Leu Ser Asp Arg Ala Lys Glu Ala
                165                 170                 175

Lys Glu Phe Leu Val Gln Leu Arg Asn Met Val Gln Ile Gln Glu
            180                 185                 190

Asn Ser Val Glu Phe Glu Ala Cys Leu Val Ala Gln Cys Asp Ala Leu
        195                 200                 205

Ile Asp Ala Leu Asn Arg Arg Lys Ala Gln Leu Leu Ala Arg Val Asn
    210                 215                 220

Lys Glu His Glu His Lys Leu Lys Val Val Arg Asp Gln Ile Ser His
225                 230                 235                 240

Cys Thr Val Lys Leu Arg Gln Thr Thr Gly Leu Met Glu Tyr Cys Leu
                245                 250                 255

Glu Val Ile Lys Glu Asn Asp Pro Ser Gly Phe Leu Gln Ile Ser Asp
            260                 265                 270

Ala Leu Ile Arg Arg Val His Leu Thr Glu Asp Gln Trp Gly Lys Gly
        275                 280                 285

Thr Leu Thr Pro Arg Met Thr Thr Asp Phe Asp Leu Ser Leu Asp Asn
    290                 295                 300

Ser Pro Leu Leu Gln Ser Ile His Gln Leu Asp Phe Val Gln Val Lys
305                 310                 315                 320

Ala Ser Ser Pro Val Pro Ala Thr Pro Ile Leu Gln Leu Glu Glu Cys
                325                 330                 335

Cys Thr His Asn Asn Ser Ala Thr Leu Ser Trp Lys Gln Pro Pro Leu
```

-continued

```
                    340                     345                     350
Ser Thr Val Pro Ala Asp Gly Tyr Ile Leu Glu Leu Asp Asp Gly Asn
        355                     360                     365

Gly Gly Gln Phe Arg Glu Val Tyr Val Gly Lys Glu Thr Met Cys Thr
    370                     375                     380

Val Asp Gly Leu His Phe Asn Ser Thr Tyr Asn Ala Arg Val Lys Ala
385                     390                     395                 400

Phe Asn Lys Thr Gly Val Ser Pro Tyr Ser Lys Thr Leu Val Leu Gln
                405                     410                     415

Thr Ser Glu Gly Lys Ala Leu Gln Gln Tyr Pro Ser Glu Arg Glu Leu
                420                     425                     430

Arg Gly Ile
        435
```

CELL REGULATION FACTOR TTO 20

FIELD OF THE INVENTION

The present invention relates to the cell regulation factor TTO 20 and DNA therefor, and its preparation and use for screening purposes for the discovery of modulators for TTO 20 activity.

BACKGROUND

The many biological effects of interleukin-1 (IL-1) include the action of IL-1 on the metabolism of many types of cells from the connective tissue. An example of cells of this type is articular chondrocytes. IL-1 inhibits the synthesis of proteoglycans (PG) by chondrocytes and stimulates the production of prostaglandin $E_2$ and metalloproteinases, which are capable of degrading molecules of the extracellular matrix.

On the basis of experimental results, and the discovery of IL-1, PG fragments, and proteolytic enzymes in inflammation-modified joints, it was concluded that IL-1 plays a part in cartilage degradation in osteoarthrosis and rheumatoid arthritis (Beuton H P & Tyler J A, 1988, *Biochem. Biophys. Res. Comm.* 154:421–428; Aydelotte M B et al., *Comm. Tiss. Res.* 28:143–159; Wood D D et al., *Arthritis Rheum.* 26:975–983; Lohmander L S et al., *Trans. Orthop. Res. Soc.* 17:273). Matrix metalloproteases are potential candidates for starting points for a therapy with active compounds that interact with these enzymes. Until now, no actual molecular starting points have been identified that relate to early steps in the complex process that leads to cartilage degradation. For this reason, various approaches have been chosen in order to obtain molecular starting points of this type for a medicinal therapy of osteoarthrosis and rheumatoid arthritis.

Such an approach is described in European Patent Application EP 0 705 842 A2. The question was whether it would be possible to obtain potential molecular starting points for a medicinal therapy of IL-1β-induced cartilage degradation on the RNA plane in human, articular chondrocytes from osteoarthritic cartilage.

For this purpose, genes were identified that are expressed differentially in diseased cartilage. Total RNA from IL-1β stimulated and nonstimulated human chondrocytes was subjected to a differential display of mRNA by reverse transcription and the polymerase chain reaction (DDRT-PCR). This method can be used for the identification and isolation of genes that are expressed differentially in two cell populations (Liang P & Gardee A B (1992), *Science* 257: 967–971; Liang P et al., A B (1993), *Nucl. Acids Res.* 21: 3269–3275; Bauer D et al. (1993), *Nucl. Acids Res.* 21:4272–4280). The key element of this technology is the use of a set of oligonucleotide primers, one of which binds to the polyadenylated tail of the mRNA, and the others are random decamers that bind to various other sites of the mRNA. Such mRNA subpopulations, which are defined by a specific set of primers, are amplified after reverse transcription and separated on DNA sequencing gels. Band patterns are seen that are characteristic for one of each of the cell lines studied. Thus, for example, 100 different primer combinations should afford 10,000 different PCR products, which represent at least approximately half of all the genes expressed in a cell line. A comparison of the band patterns of two different cell lines indicates those bands that correspond to differentially expressed genes. On the basis of this information, it is now possible to extract, to reamplify, to subclone, and to sequence bands of differentially expressed gene products from the gel.

However, this is to be qualified by saying that this method has a number of difficulties:

1. As a result of the high sensitivity of the DDRT-PCR, slightly artificial bands can result.
2. The analysis of complex gene expression patterns is difficult.
3. Only tiny amounts of RNA are available as starting material.

These difficulties cause uncertainty in the results obtained.

In European Patent Application EP 0 705 842 A2, a number of short DNA sequences are disclosed that have been identified in the manner described above. An analysis of these sequences showed that some are complete or have very great identity with the sequences of already known genes. Thus, a cDNA fragment having 100% identity with human osteopontin, another cDNA fragment having 97.2% identity with human calnexin, and a further fragment having 99.5% identity with human TNF-30 stimulated gene 6 (TSG-6) were found. Most of the fragments found, however, could not be assigned to any known gene based on the sequence corresponding to the fragment. This group of cDNA fragments also included the 400 bp-long clone TTO 20/2(2), 152 bp of which has been deciphered.

In the context of the present invention, the clone TTO 20/2 has now been investigated more closely. An antisense experiment is one method for investigating the functional meaning of the corresponding gene or gene product.

The expression of antisense RNA in human chondrosarcoma cells, which are regarded as model cells for cartilage differentiation, yielded indications of a role of TTO 20/2. The antisense approach is based on transforming the cultured cells with a vector that expresses antisense mRNA to TTO 20, but at the same time, the vector also expresses an indicator protein whose activity indicates whether antisense RNA was formed. Vectors of this type are called bicistronic or dicistronic vectors. The starting vector for the present constructs was pED4, whose construction has been described by Kaufmann et al. (Kaufmann et al., (1991), *Nucl. Acids Res.* 19: 4485–4490).

In antisense technology, the formation of a functional protein is restricted or even prevented via the expression of a complementary RNA (antisense RNA) that binds to the protein-encoding mRNA (sense RNA). In particular, as the present examples confirm, antisense RNA can be employed for subregions of the encoding mRNA, and for the 3' or 5' untranslated region, in order to prevent the formation of the target protein. With the aid of the vector, EST fragments that have no defined open reading frame can thus be used in order to work out the action of the protein that is finally encoded by the associated gene because the "antisense-expressed" EST switches off or decreases the reading of the encoding sense mRNA. If the synthesis of the target protein that is blocked in this way plays an important role in the cell, this has direct or indirect effects on cell division, cell growth, synthesis of regulated and expressed proteins etc. If the antisense expression prevents, for example, the formation of a factor that plays a role in signal cascades, then that cascade is disturbed.

If the factor is a transcription factor, the expression of a number of genes is disturbed. This can be recognized, for example, from morphologically visible changes that can be attributed to altered expression of secreted proteins, particularly proteases.

The genes, or products thereof, identified in this way can be employed as therapeutic targets for the search for pharmacologically active substances. Likewise, cells transformed in this way can be used in screening systems attempting to block the action of the antisense RNA.

DNA chip technology allows the direct analysis of such changes because the transcript profiles of transformed cells can be compared with untransformed or mock-transformed cells. The comparison then allows conclusions to be drawn as to whether an EST plays a crucial role in the context of a clinical picture and is thus suitable as a screening target. The use of the vector is thus also suitable for the discovery of novel targets and for the profiling of novel medicaments. The vector is particularly suitable for the synthesis of HTS systems for target validation. Expediently, EST clones are cultured in HTS formats, such as 96-well microtiter plates, and the insert DNA is amplified by means of PCR using suitable PCR primers that, for example, generate a PST cleavage site on the 3' side and an Eco RI cleavage site on the 5' side for cloning in one of the pED4 derivatives described. In a second step, the PCR fragments generated in this way are cleaved using PstI and Eco RI and ligated into the dicistronic EGFP vector. The screening format here is retained. The ligated construct containing a PCR fragment is pipetted onto previously prepared eukaryotic cells, using commercially obtainable pipetting robots, along with suitable transfection agents, such as $CaPO_4$, Fugene 6 (manufacturer: Boehringer, Mannheim; lipofectamine, Life Technologies, Eggenstein) or others, and the cells are transformed according to customary processes. Here too, the screening format is retained. The cells are incubated in the presence of $CO_2$ according to customary processes and tested for fluorescence emission after 24–72 hours under automated conditions in a fluorescence scanner. Wells with transformed, fluorescent cells are then evaluated for changes in growth and changes in cell morphology, etc., as compared with transformed control cells that were transfected with the vector lacking a PstI-Eco RI insert. If changes of this type occur, this indicates an essential action of the expressed antisense RNA. The isolation of the cloned DNA and the subsequent sequence analysis give an indication of the nucleotide sequence and thus the gene or the coded protein involved. In this way, the first functional indications of gene activities can be found whose function cannot itself be derived by means of the EST.

SUMMARY OF THE INVENTION

The invention therefore relates to the TTO 20 polypeptide comprising the amino acid sequence according to Table 1, SEQ. ID. NO.:10.

A further object of the invention is a substantially purified TTO 20 polypeptide, wherein said polypeptide is encoded by a polynucleotide comprising the nucleic acid sequence of SEQ. ID. NO. 9 or degenerate variants thereof.

A further object of the invention is a substantially purified TTO 20 polypeptide, wherein said polypeptide is encoded by a polynucleotide that is at least 80% identical to the nucleic acid sequence of SEQ. ID. NO. 9 or degenerate variants thereof, preferably 85% identical to the nucleic acid sequence of SEQ. ID. NO. 9, more preferably 90% identical to the nucleic acid sequence of SEQ. ID. NO. 9 , and most preferably 95% identical to the nucleic acid sequence of SEQ. ID. NO. 9.

Another object of the invention is an isolated polynucleotide comprising the nucleotide sequence of SEQ ID NO.: 9, preferably base pair 1 to base pair 1305.

A further object of the invention is a polynucleotide having a nucleic acid that is at least 80% identical to the nucleotide sequence of SEQ. ID. NO. 9 or degenerate variants thereof, preferably 85% identical to the nucleic acid sequence of SEQ. ID. NO. 9, more preferably 90% identical to the nucleic acid sequence of SEQ. ID. NO. 9, and most preferably 95% identical to the nucleic acid sequence of SEQ. ID. NO. 9.

Another object of the invention is an antibody that recognizes the polypeptide of TTO20 comprising the amino acid sequence according to Table 1, SEQ. ID. NO.:10.

Another object of the invention is an expression vector construct comprising the polynucleotide of SEQ ID NO 9 and a host cell transfected or transformed with the expression vector construct.

Another object of the invention is a process for the preparation of the TTO 20 polypeptide comprising the steps of:

(a) culturing a host cell under conditions that result in the expression of said TTO 020 polypeptide; and (b) isolation of said TTO 20 polypeptide from said host cell or culture medium.

A further object of the invention is a TTO 20 polypeptide prepared by this process.

Another object of the invention is a process for the identification of cell lines, cells, or tissues that express the TTO 20 polypeptide, wherein a nucleic acid probe is used to hybridize an RNA fragment derived from SEQ ID NO 9 in a biological sample.

A further object of the invention is a method for determining the complete polynucleotide sequence of the TTO20 polypeptide comprising the use of hybridization and/or PCR processes.

A further object of the invention is a method comprising the determination of the three-dimensional structure of the TTO 20 polypeptide and using said three-dimensional structure to design inhibitors or activators of said TTO 20 polypeptide.

A further object of the invention is a method for determining substances that influence the activity of TTO20 comprising an assay that measures the amount of TTO 20 polypeptide.

Another object of the invention is a diagnostic kit for the diagnosis of inflammatory disorders, preferably rheumatoid arthritis, comprising an antibody.

Another object of the invention is a diagnostic kit for the diagnosis of inflammatory disorders, preferably rheumatoid arthritis, comprising a polynucleotide of SEQ ID NO 9.

DETAILED DESCRIPTION OF THE INVENTION

EXAMPLE 1

Identification of cDNAs Using the TTO20/2 Sequence

The partial sequence of 152 bp designated by TTO20/2 is disclosed in European Patent Application EP 0 705 842 A2. In order to obtain information about the complete cloned sequence, the entire DNA of TTO 20/2 was sequenced with the aid of the SP 6 primer. The sequencing reactions were carried out according to the chain termination DNA sequencing method as described in Sanger et al. (Sanger, F. et al. (1977), *Proc. Natl. Acad. Sci. USA* 74:5463–5467). From the sequencing, a total length for the cloned insert of 272 bp resulted. Using this sequence, a homology search was carried out in the gene bank (NCBI) and the EMBL database. To do this, the BLAST and FASTA algorithms were used, which are part of the GCG DNA analysis package of the Genetics Computer Group, Madison, USA.

The homology search showed significant similarities to two EST clones in the public database having the gene bank accession number M 51303 (sequence ID: g192469) and the accession number H 05077 (sequence ID: g868629). The corresponding clones having clone ID 283071 or 43508 were ordered from Genome Systems, St. Louis, USA, and completely sequenced. The clone having clone ID 283071 showed the largest insert of about 2580 bp, the clone having clone ID 43508 is markedly smaller with an insert size of 2200 bp, but has 100% sequence homology with clone 283071. The complete sequence of clone 283071 is shown in Table 1 and begins at nucleotide 706.

EXAMPLE 2

Identification of an Open Reading Frame

With the aid of the Translate program from the GCG analysis package, the sequenced DNA of clone 283071 was investigated for the occurrence of open reading frames (ORF). Accordingly, an open reading frame that codes for 200 amino acids is found at the 5' end of the sequence. Following the stop codon TAA, an untranslated region of about 1950 bp long is found, followed by a polyadenylation signal, and ending with a Poly A tail. The sequence corresponds to the sequence indicated in Table 1 from nucleotide 706 to nucleotide 3262.

A homology search was carried out in public databases using the 5' DNA sequence and using the protein sequence that encompasses the open reading frame. This showed that the open reading frame is perfectly homologous with a sequence encoding 184 amino acids, which is localized on a cDNA by the name of KIAA0282 (gene bank accession number: g87458). The homology to KIAA0282 ends abruptly after the amino acid sequence LQTSEG and is restricted to the nucleotide level at 552 bp. The reading frame in clone 283071 continues for 15 amino acids and is then ended with a TAA stop codon.

Figure 1:
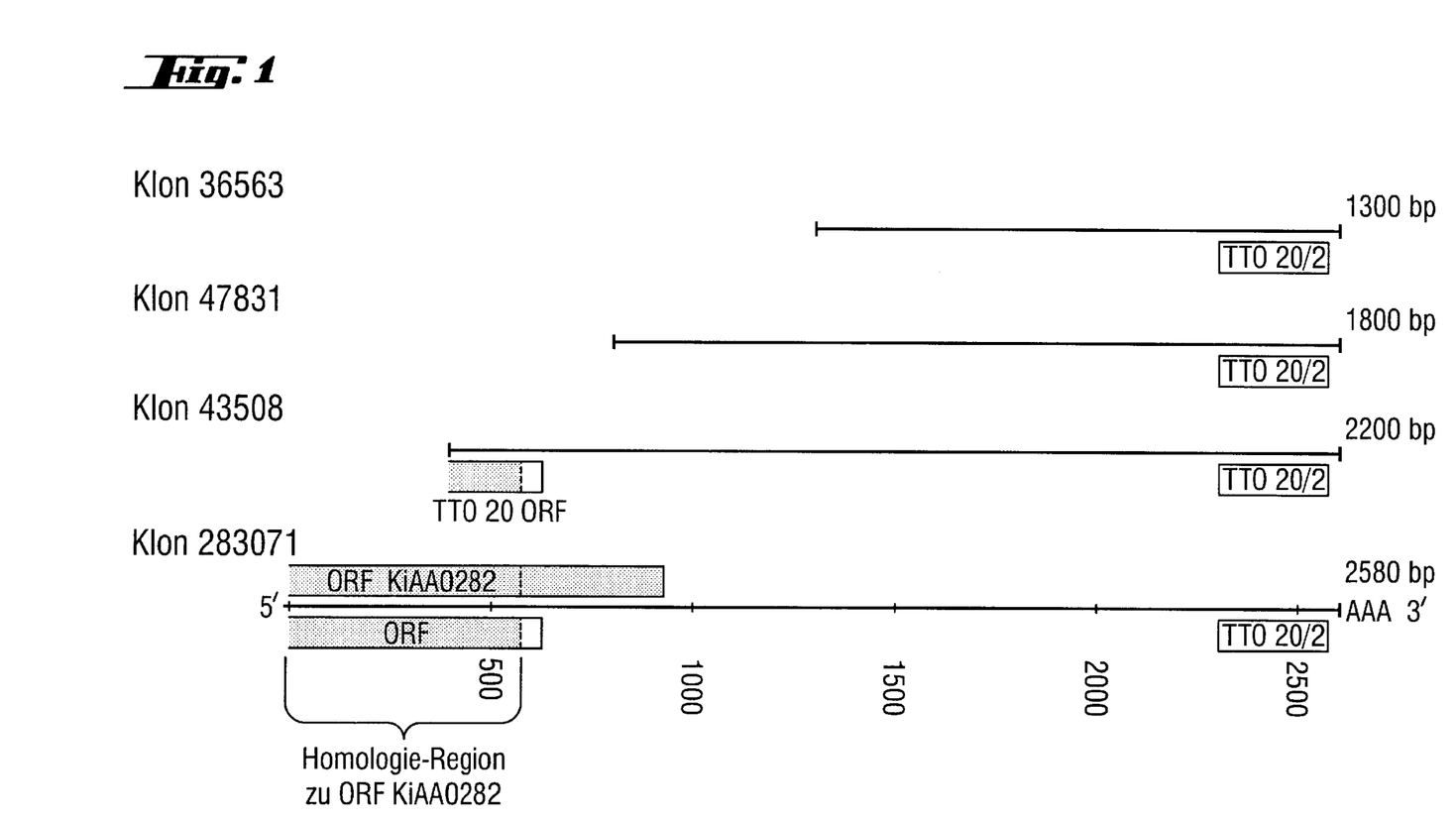
FIG. 1 depicts the schematic representation of clones 283071, 43508, 47831, and 36563, as well as the open reading frame ("ORF") of KiAA0282 and TTO20 (Klon means Clone and "Homologie-Region zu" means "Region of homology to").

However, the reading frame in the KIAA0282 ORF continues for 123 amino acids. This region and the complete 3' untranslated region of about 2000 bp of the KIAA0282 sequence are different from the sequence of clone 283071. For illustration, see FIG. 1.

EXAMPLE 3

Verification of the Binding of the 3' Region of TTO20 to the 5' Region of Kiaa0282

In order to confirm that the 5'-coding region of the ORF of KIAA0282 is linked to the 3' region of TTO20, further publicly accessible EST clones were sequenced. In addition to the above mentioned clone 43508, these also include clone 47831 and clone 36563, which are obtainable from Genome Systems. The sequences clearly confirm the correctness of the sequence determined for TTO20.

In order to make clear the connection between the 5' region of KIAA and the 3'region of TTO20 using an independent process, the following PCR strategy was chosen. Two forward primers were derived from the 5' region of KIAA0282; Primer 1: 5'-CAACTCC TGTAT CACC-3' (SEQ ID NO.:1), and Primer 2: 5'-AGTGCGATGTCTTCTACTG-3' (SEQ ID NO.: 2). The backward primers 3 and 4 were derived from the 3' region of clone 283071. Primer 3: 5'-TCTAAAGGCAG GAGAGGAAC-3' (SEQ ID NO.: 3). Primer 4: 5'-TTCATGTGTCTTGCTTACTC-3' (SEQ ID NO.: 4). In a connected region, a fragment of size 2097 bp would have to be amplifiable using the primers 1 and 4, and a fragment 1211 bp in size using the primer pair 2 and 3. These DNAs were used as matrices for the polymerase chain reaction: brain cDNA from the Multiple Tissue cDNA Panel Human 1 (order number: K1420-1, Clontech, Heidelberg, Germany) and fetal brain cDNA from the Human Fetal cDNA Panel (order number: K1425-1, Clontech, Heidelberg, Germany). 0.5–1 µl aliquots were introduced into a PCR reaction with the primer pair 1 and 4. The PCR reaction was carried out as follows using the buffer recommended by the manufacturer of the enzymes: polymerase mixture: 19 parts of AmpliTaq DNA polymerase (Perkin-Elmer, Weiterstadt, Germany) and 1 part of pfu polymerase (Stratagen, La Jolla, USA). Primer concentration: 10 pM. DNA Cycler (Perkin Elmer, Model 480). PCR conditions for one cycle: 94° C., 2 min.; 94° C., 30 sec.; 59° C., 30 sec.; 72° C., 30 sec.; 72° C., 7 min, reaction volume: 50 µl. After 25–50 cycles the reaction was cooled to 4° C. and the reaction mixture was analysed in a 1.2% strength agarose gel. It was possible to amplify the corresponding PCR fragment of the size of about 2100 bp both from the brain cDNA and from the fetal brain cDNA. If 0.5–1 µl aliquots of these samples are employed in a further, "nested" PCR reaction using identical conditions, but with the primers 2 and 3, a PCR fragment of a size of 1200 bp results. This clearly indicates the presence of a cDNA having a homologous 5' region of KIAA0282 and the 3' region of TTO20.

For further confirmation, the DNA fragment 2100 bp in size was excised from the agarose gel and the DNA was eluted electrophoretically (Ausubel et al.). The eluted DNA was taken up in 10 µl of sterile water and cloned into the vector pCR2.1 according to the recommendations of the manufacturer (Invitrogen BV, Groningen, Holland). The cloning of the PCR fragments was carried out with the aid of the TA cloning kit of the same manufacturer using the procedure specified by the manufacturer.

The sequencing of the cloned DNA fragment was carried out by the chain termination method according to Sanger et al. with the aid of the dye terminators and a model 377 sequencer (Perkin Elmer, Langen, Germany). The sequencing exactly confirms the finding obtained by PCR analysis. Accordingly, the sequence indicated in Table 1 (nucleotides 685 to 3262) can be extended on the 5' side by the DNA sequence specified by KIAA0282. The complete sequence is shown in Table 1 (nucleotides 1 to 3262).

EXAMPLE 4

Indications of Function

The origin of the ESTs from various tissues indicate an involvement of the expressed gene in inflammatory processes. The RNA analyses (see EP-A 0 705 842) confirm a more than four-fold induction of the expression of the gene in interleukin 1β-stimulated chondrocytes. On the basis of the bioinformatic analyses, the discoverers of the cDNA for KIAA0282 propose a homology of the encoded protein with a zinc finger protein. Zinc finger proteins can act as transcription factors, i.e., play an essential role in the regulation of the cell process. In order to obtain immediate information about a possible function of TTO20, an antisense expression set with a subregion of the sequence (nucleotide 705–nucleotide 3198 of Table 1) was selected. This range includes both part of the coding and the non-coding 3' region of the cDNA.

4.1. Construction of the Antisense Expression Vector

Figure 2:
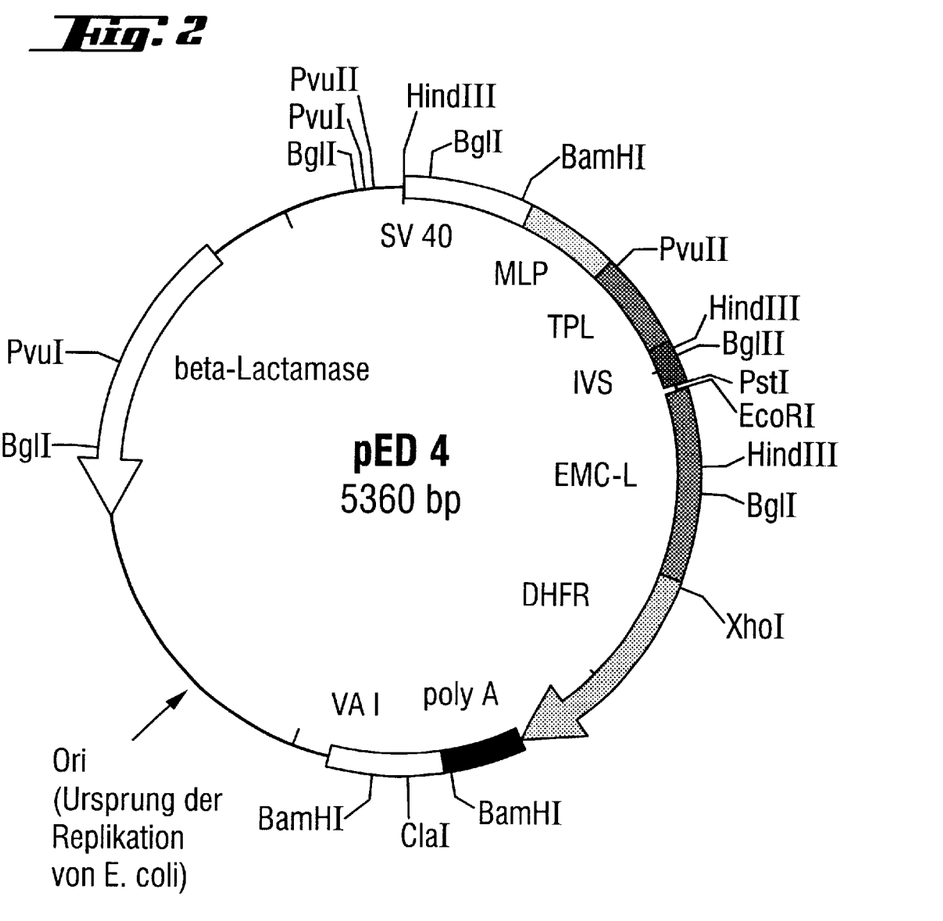
FIG. 2 depicts the schematic representation of the plasmid pED4, abbreviations: SV40=SV40 enhancer and origin of replication; MLP=adenovirus "Major Late" promotor; TPL= leader sequence "Adenovirus Major Late" mRNA; IVS= selection marker dihydrofolate reductase; polyA=SV40 polyadenylation signal; VA I=adenovirus VA I RNA gene. ("Ursprung der Replikation von E. coli" means "Origin of replication of E. coli").

The starting vector chosen was the dicistronic vector pED 4 (FIG. 2; Kaufman et al., *Nucleic Acids Research* 19:448–4490 (1991)). For this vector, whose construction is described in detail in Kaufman et al. and whose precursor plasmid pMT2 is obtainable under the No. ATCC 67122 at the ATCC, it has already been shown that antisense RNA can be expressed via the first cistron. The vector contains the following structural elements: replication origin for replication in eukaryotic cells, the SV40 expression enhancer, the adenovirus Major Late Promotor, the leader sequence of the Adenovirus Major Late Messenger RNA, a hybrid intron with a splice site, the encephalomyocarditis virus leader sequence, the selection marker dihydrofolate reductase, the SV40 polyadenelation signal, the adenovirus V1 RNA gene, a replication origin and a selection marker for the replication of the vector in recombinant *E. coli*. In a first step, the selection marker dihydrofolate reductase should then be exchanged for the gene for the green fluorescent protein (GFP). The expression of the GFPs via the second cistron thus serves in transient expression experiments as a visible measure of the expression of the antisense construct.

Isolated plasmid DNA from pED4 was cleaved using the restriction endonucleases Cla1 and Xho1. For the isolation of the gene for GFP, DNA of the commercially obtainable vector pEGFP (Clontech, Heidelberg, Germany) was cleaved using the restriction enzymes Sal1 and Not1. The DNA fragments were separated by gel electrophoresis. Because a single Cla1 cleavage site lies about 350 bp downstream of the coding dihydrofolate reductase sequence in the VA gene, a third fragment is needed for the restoration of the PolyA region and of the VA gene section. By means of PCR, a DNA fragment from the vector pED4 was amplified, which contained an Not1 cleavage site at the 5' end and a Cla1 cleavage site at the 3' end and which comprised the still missing sequence of the PolyA region and of the VA gene.

Primers used:
  Forward primer Not L:
    5'-ATAAGAATGCGGCCGCTAAACTATCAGGA
    AGATGCTTTCAAGTTC-3' (SEQ ID NO.: 5)
  Backward primer Cla R:
    5'-ACAGGCTCTCCTTTTGCAC-3' (SEQ ID NO.: 6)

Figure 3:
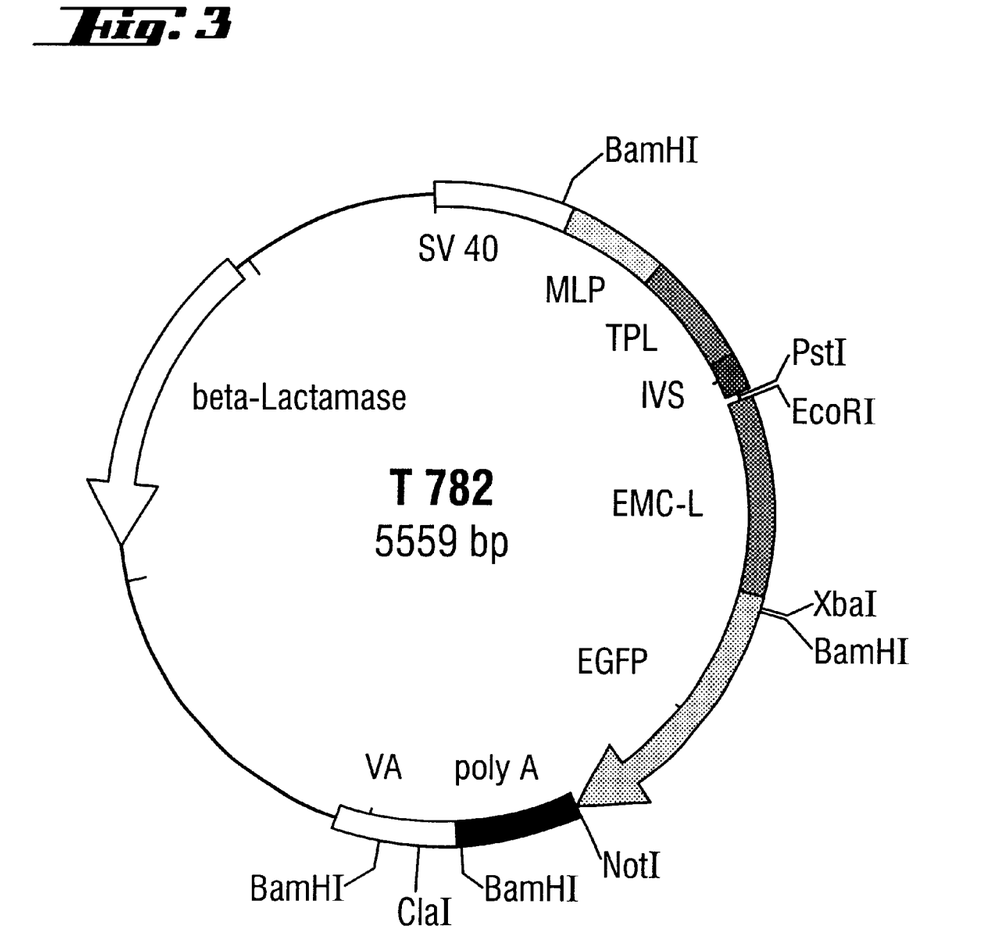
FIG. 3 depicts the schematic representation of the plasmid T 782, abbreviations: SV40=SV40 enhancer and origin of replication; MLP=adenovirus "Major Late" promotor; TPL= leader sequence "Adenovirus Major Late" mRNA; IVS= intron hybrid with splice site; EMC-L= encephalomyocarditis leader sequence; EGFP=enhanced green fluorescent protein; polyA=SV40 polyadenylation signal; VA=adenovirus VA RNA gene.

The PCR product was digested with Not1 and Cla1, separated from nucleotides by gel electrophoresis and isolated. The three fragments were pipetted together in equimolar ratio, mixed with buffer, ATP and T4 ligase and ligated. The ligation mixture was transformed in *E. coli* DH5 α cells and plated out on ampicillin selection plates. After isolation of the plasmid DNA from transformants, the DNAs were checked for their fragment size by means of a BamH1 restriction digestion. The original vector pED4 has three BamH1 cleavage sites, which afford three DNA fragments of sizes of about 2950 bp, 2190 bp and 220 bp. As a result of the gene exchange, the novel vector T782 has four BamH1 cleavage sites that when digested with BamH1 lead to four DNA fragments of about 2950 bp, 1315 bp, 1075 bp and 220 bp. The correct sequence of the newly integrated indicator gene was confirmed by sequencing. The plasmid map of the vector T782 is shown in FIG. 3.

For the antisense expression of the RNA of TTO20, the TTO20 sequence was amplified with the aid of PCR and appropriate primers and cloned into the GFP vector T782 via the Eco R1 cleavage site.

Primers used:
  Forward primer:
    5'-GGAATTCGATCAGATCTCTCACTGCAC-3'
    (SEQ ID NO.: 7)
  Backward primer:
    5'-GGAATTCACTTCTGTGCAGTAACAGAG-3'
    (SEQ ID NO.: 8)

Figure 4:
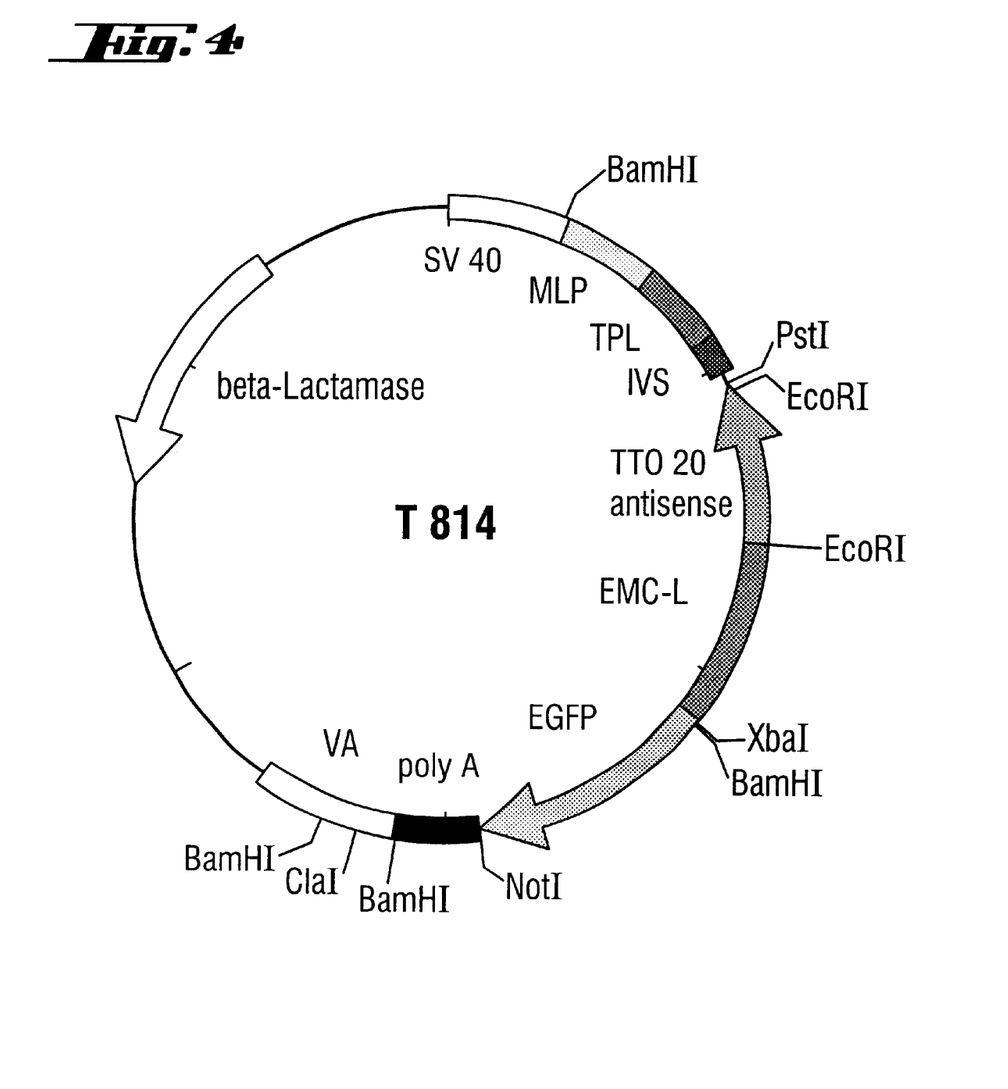
FIG. 4 depicts the schematic representation of plasmid T 814, for abbreviations see FIG. 3 description.

The resulting fragment of size about 2500 bp was completely digested using the restriction enzyme Eco R1, separated by gel electrophoresis and isolated. The isolated fragment was cloned into the GFP vector, which was likewise cleaved with Eco R1. In order to ensure that the fragment cloned was in the antisense direction, various recombinant clones were cleaved using the restriction enzyme Pst1 after transformation of *E.coli* DH5 α and the fragments were analyzed by gel electrophoresis. Owing to the fact that a single Pst1 cleavage site is made available for the Eco R1 cloning site by means of the vector, a Pst1 fragment about 310 bp in size additionally results with the correct orientation of the DNA fragment in the vector, while a fragment about 810 bp in size is missing in the pattern of the Pst fragments. The plasmid map of the bicistronic antisense vector T814 is shown in FIG. 4.

4.2. Transfection of Human Chondrosarcoma Cells using the Antisense Vector

Chondrosarcoma cells are therefore of particular interest, because they can serve as a model for joint disorders. The adherently growing chondrosarcoma cells were grown in culture flasks (75 cm²) containing 20 ml of Dulbecco's MOD Eagle Medium (DMEM with 4.5 g of glucose/L) and the following additives: 10% fetal calf serum, 200 mM L-glutamine, 5 mM sodium pyruvate, 20 mM Hepes buffer pH 7.2, 0.02 µg/ml of hydrocortisone, 0.1 µg/ml of insulin, 0.025 mg/ml of ascorbic acid and 0.05 mg/ml of gentamycin. Every 3–4 days, the cells were detached from the culture flasks by trypsinization, taken up in 10 ml of fresh culture medium, freed from the trypsin by centrifugation, diluted in the ratio 1:5–1:10 and reinoculated. For trypsinization, trypsin/EDTA was used in a concentration of 0.25% trypsin and 1 mM EDTA. 1 ml of this solution remained on the cells for 2–5 minutes at 37° C. The stock culture of chondrosarcoma cells was stored at −80° C. in 10% DMSO and 90% of the culture medium.

For the transfection of DNA in chondrosarcoma cells, various methods were tested, among them the calcium phosphate method, the DEAE-dextran method, liposomemediated transfection methods, use of activated dendrimers, and electroporation. The best transfection rates were achieved when the transfection agent used was Fugene 6 (Boehringer Mannheim, Mannheim, Germany).

Between $2\times10^5$ and $4\times10^5$ cells were inoculated into 1 well each of a 6-well cell culture plate (Becton & Dickinson, Heidelberg, Germany). The cells were in about 2 ml of nutrient solution. 0.5–2 µg each of DNA that was isolated and purified with the aid of the Qiafilter Plasmid Midikit (Qiagen, Hilden, Germany) were employed for the transfection. For this, the cells were first incubated with 5% $CO_2$ for 18–24 h at 37° C. in an incubator. The cells should be grown to 50–80% confluence. Best transfection rates are achieved when $4\times10^5$ cells/well are inoculated, and 2 µg of DNA and 6 µl of Fugene/100 µl of serum-free medium are used. The transfection was carried out according to the instructions of the manufacturer.

4.3. Antisense Expression in Chondrosarcoma Cells

The transformed chondrosarcoma cells were first tested over a period of 16 48 hours after transfection for the appearance of the green fluorescence that takes place due to the expression of the green fluorescent protein GFP. Even after 16 hours, green fluorescent cells can be detected after fluorescence excitation, which markedly increased over a period of 20 h.

For the detection of the antisense RNA formed, cells from two wells in each case of a 6-well plate were used. For the isolation of the RNA, an RNeasy Miniprep Kit from Qiagen (Hilden, Germany) was used according to the instructions of the manufacturer. The RNA samples were taken up in 30 µl of RNase-free water and stored at −20° C. The RNA was analyzed with the aid of Northern blots (Ausubel, F. M. et al. Current Protocols in Molecularbiology, Vol. 1–3, John Wiley and Sons, New York, 1997) using digoxygenin-labeled DNA sample. The labeling of the DNA was carried out in a PCR reaction by means of the DIG Probe Synthesis Kits from Boehringer (Mannheim, Germany). The matrix used was the previously purified PCR fragment containing the TTO20 portion about 2.5 kb in size, which was freed from the nucleotides. On hybridization with this probe, the expression of the antisense RNA in the transfected chondrosarcoma cells becomes clearly visible in a time-dependent manner.

Compared with non-transformed chondrosarcoma cells, the cell form of the transformed cells is not markedly changed. However, an unequal distribution of the GFP fluorescence is visible compared with the control transfection. The control was carried out using a corresponding vector, which instead of TTO20 antisense contained the antisense RNA of cofilin, a cytoskeleton-regulating protein. The spotty fluorescence distribution suggests that the cytoskeleton of the cells is modified compared with the controls. This indicates a direct function of the expressed antisense RNA on the suppression of the protein formed from TTO20.

TABLE 1

TTO 20-2 gene from 1 to 3262

```
  1 GCCCTGGCCCCGGTGCCCCGCAACTCCTGTATCACCTGCCCCCAGTGTCACCGCAGCCTC
  1 A   L   A   P   V   P   R   N   S   C   I   T   C   P   Q   C   R   R   S   L   -
 61 ATCCTGGATGACCGGGGGCTCCGCGGCTTCCCCAAGAATCGCGTACTGGAAGGGGTAATT
 21 I   L   D   D   R   G   L   R   G   F   P   K   N   R   V   L   E   G   V   I   -
121 GACCGCTACCAGCAGAGCAAAGCCGCGGCCCTCAAGTGCCAGCTCTGCGAGAAGGCGCCC
 41 D   R   Y   Q   Q   S   K   A   A   A   L   K   C   Q   L   C   E   K   A   P   -
181 AAGGAAGCCACCGTCATGTGCGAACAGTGCGATGTCTTCTACTGCGATCCGTGCCGCCTG
 61 K   E   A   T   V   M   C   E   Q   C   D   V   F   Y   C   D   P   C   R   L   -
241 CGCTGCCACCCGCCCCGGGGGCCCCTAGCCAAGCACCGCCTGGTGCCCCCGGCCCAGGGT
 81 R   C   H   P   P   R   G   P   L   A   K   H   R   L   V   P   P   A   Q   G   -
301 CGTGTGAGCCGGAGGCTGAGCCCACGCAAGGTCTCCACCTGCACAGACCACGAGCTGGAG
101 R   V   S   R   R   L   S   P   R   K   V   S   T   C   T   D   H   E   L   E   -
361 AACCACAGCATGTACTGCGTGCAATGCAAGATGCCCGTGTGCTACCAGTGCTTGGAGGAG
121 N   H   S   M   Y   C   V   Q   C   K   M   P   V   C   Y   Q   C   L   E   E   -
421 GGCAAACACTCCAGCCACGAAGTCAAGGCTCTGGGGGCCATGTGGAAACTACATAAGAGC
141 G   K   H   S   S   H   E   V   K   A   L   G   A   M   W   K   L   H   K   S   -
481 CAGCTCTCCCAGGCGCTGAACGGACTGTCAGACAGGGCCAAAGAAGCCAAGGAGTTTCTG
161 Q   L   S   Q   A   L   N   G   L   S   D   R   A   K   E   A   K   E   F   L   -
541 GTACAGCTGCGCAACATGGTCCAGCAGATCCAGGAGAACAGTGTGGAGTTTGAAGCCTGT
181 V   Q   L   R   N   M   V   Q   Q   I   Q   E   N   S   V   E   F   E   A   C   -
601 CTGGTGGCCCAATGTGATGCCCTCATCGATGCCCTCAACAGAAGAAAAGCCCAGCTGCTG
```

TABLE 1-continued

TTO 20-2 gene from 1 to 3262

```
201 L   V   A   Q   C   D   A   L   I   D   A   L   N   R   R   K   A   Q   L   L   -
661 GCCCGCGTCAACAAGGAGCATGAGCACAAGCTGAAGGTGGTTCGAGATCAGATCTCTCAC

221 A   R   V   N   K   E   H   E   H   K   L   K   V   V   R   D   Q   I   S   R   -
721 TGCACAGTGAAATTGCGCCAGACCACAGGT6TCkTGGAGTACTGCTTGGAGGTGATTAAG

241 C   T   V   K   L   R   Q   T   T   G   L   M   E   Y   C   L   E   V   I   K   -
781 GAAAATGATCCTAGTGGTTTTTTGCAGATTTCTGACGCCCTCATAAGAAGAGTGCACCTG

261 E   N   D   P   S   G   F   L   Q   I   S   D   A   L   I   R   R   V   H   L   -
841 ACTGAGGATCAGTGGGGTAAAGGCACACTCACTCCAAGGATGACCACGGACTTTGACTTG

281 T   E   D   Q   W   G   K   G   T   L   T   P   R   M   T   T   D   F   D   L   -
901 AGTCTGGACAACAGCCCTCTGCTGCAATCCATCCACCAGCTGGATTTCGTGCAAGTGAAA

301 S   L   D   N   S   P   L   L   Q   S   I   H   Q   L   D   F   V   Q   V   K   -
961 GCTTCCTCTCCAGTCCCAGCAACCCCTATCCTACAGCTGGAGGAATGTTGTACCCACAAC

321 A   S   S   P   V   P   A   T   P   I   L   Q   L   E   E   C   C   T   H   N   -
1021 AACAGCGCTACGTTGTCCTGGAAACAGCCACCTCTGTCCACGGTGCCCGCCGATGGATAC

341 N   S   A   T   L   S   W   K   Q   P   P   L   S   T   V   P   A   D   G   Y   -
1081 ATTCTGGAGCTGGATGATGGCAACGGTGGTCAATTCCGGGAGGTGTATGTGGGGAAGGAG

361 I   L   E   L   D   D   G   N   G   G   Q   F   R   E   V   Y   V   G   K   E   -
1141 ACAATGTGCACTGTGGATGGTCTTCACTTCAACAGCACATACAACGCTCGGGTCAAGGCC

381 T   M   C   T   V   D   G   L   H   F   N   S   T   Y   N   A   R   V   K   A   -
1201 TTCAACAAAACAGGAGTCAGCCCGTACAGCAAGACCCTGGTCCTCCAAACGTCTGAGGGT

401 F   N   K   T   G   V   S   P   Y   S   K   T   L   V   L   Q   T   S   E   G   -
1261 AAGGCCCTTCAGCAGTATCCCTCAGAGCGAGAACTGCGTGGCATCTAAAGTGGCTGGCAA

421 K   A   L   Q   Q   Y   P   S   E   R   E   L   R   G   I   *        (SEQ ID NO.: 10)
1321 GCCCGGAGGTAACCCCACCACTGCCCACATTCCTGAAGTGTTTCCATGACTTGCTCTGCA
1381 TTCTGCACAGAGCCGCTGTTCCTCTCCTGCCTTTAGAGAGCCTATGGTATGTGGATGTGA
1441 TCAAACCAAAGATTCCACATCGGCAGTTCCAATGGCTTGGGCCGGCGGCTTCCTTTGATA
1501 ACAATCTAAATAAGCTGCAGTTGAAGAAGCTGAAAAATGAAGGCCTGAATGTGCCCCTGG
1561 TGTGTAAGACAAATGTATCTAGGCTCTAGAGCAGGCTCCCATTCTCCACCGATACACATC
1621 ATGTGCCAGTTTTGCCCAGATGATTCTAAATTACTCTGTAGTACTTGCTTGTTCTGAGGG
1681 TGGGACCTAGGTTCTTTCCAGTCGTGGATTTGTATGACTGAATGTGTTTCAAATGGGTGG
1741 TGGGGTGCTAGAGCTGTTTAGAGAGGGCCTGTTGGCTGCTCCTGGCTTACCCACTTAGAC
1801 TGCCTCCGTTTCATACCCAAAGCGGAGGCCGTCAGCACCAGGATTGAGACTTCCTGTGGG
1861 CACCAAACAGGAAGAGACCAGCAACTTCGCATTACCCGCCATTTTCATCTTTGCCAGTCC
1921 CTTCAGTCTTGGCTAGGCTACCGAGAGCCACCATACAAGGTTCATCTCTAGAGAATTTTT
1981 GCTTCTTAGCTATACTTTAAATATTTTGGTCATCAAAGACAAGTAATGTGTCTCAGATGA
2041 GAGGCTTGAATTTGATGGCCAGATATAACCTCTGAGGCTTTTAACATTTTCATTTTAAGA
2101 GTAAGCAAGACACATGAAATTAAACCTACAAGGAGGTATTTGTGGCTGGTGCCAAAGCAT
2161 TCTGACACTTTGGGGTGTCATTTTAATCAAAGAAATCACCCCCCCACCTCACCGGGATTC
2221 TCCATAACTTCCCTCTGCAGAACTAATTATGTTGATTTTGTTCAAGTTCAAGATGTTAGC
```

TABLE 1-continued

TTO 20-2 gene from 1 to 3262

2281 TAAAAGAACTATGGTGGTGTTTTTTTTCCCACTTCCCACAAACCTCAACATGTGCCAGTC

2341 ACCCTAAAATGCTTCACATGGTTAAAAACAAGCACAATTTTGAATCCTACAGCAAGGATG

2401 AAAGGCCCCTAGCCGTGAAAACAGTGCTTTGGGGAGCAGTTGTCAGTCTAAGTGATGCTA

2461 TTCCAAGAGAAGGATATGCTGAGGGAAAATGCCCACATGACCTGTTCCCATTTGGAGTAC

2521 AGTGATGTGGTAGCTACAGCTTCCCCCAGAATTATCATTTTAGCACCTTCTCTCAGGGAT

2581 GACCTATCAGTTTGAGAGCAGTTGCCTCTTTTCTCAAAATACCATACTAACTGCTAAAGC

2641 CCTCCAAGAGTCTTTCCTAGATGCAACGCAGAAGGCCCTTGCTGGTGATGGCCTCATTTC

2701 CCATGTGTGTACAAGGTGGTTTGATTGAAGAGTGAAGTGCATGCCTGCAGAGCAGAGAGA

2761 AATTTGTAGCAATGTTGCTAATATGTGTTATCAGATCTGCGGGAAAACTATTTCTATTCA

2821 TAATACATCATGGGAATCATACTATTCTGGTAAAAATCAGTTATTAGCATAACAGCCTGA

2881 GCACTTATGTCTCTCGTTTCATCCTGCAGGAGGATGTAGCGCCTCAGTTTATTTTAATGT

2941 TCATAAGATTATGGTGTCTAATTTAATAAATTACAGGATTGGAACTGCGATCCTTGGTAC

3001 CACAGTCACAGAACTGGGGGTCATTTTCTAGATGAAACAAACGGAACAAGTTCTCTTCCA

3061 ACAAAGAAACTGTACTGTAGAAATTAATTTCCTCCATGAATTTTATATATTGTGTACAAA

3121 TATAAGGTATGTATCTGAATACAAAGAAAAGCCTATCATCATATAGATATCAGTATTCTC

3181 TGTTACTGCACAGAAGTAATTTTCTCATGATGAAATAAAGTTCACACACATACTTTCTCC

3241 ATAAAAAAAAAAAAAAAAAAAA   3262   (SEQ ID NO.: 9)

We claim:

1. An isolated polynucleotide comprising the nucleotide sequence of SEQ ID NO:9.

2. An isolated polynucleotide consisting of the nucleotide sequence of SEQ ID NO:9 from base pair 1 to base pair 1305.

3. An isolated polynucleotide encoding a TTO 20 polypeptide of SEQ ID NO:10, comprising a nucleotide sequence that is degenerate to the nucleotide sequence of SEQ ID NO:9.

4. An expression vector construct comprising the polynucleotide claimed in claim 1, 2, or 3.

5. A host cell transfected or transformed with the expression vector construct claimed in claim 4.

6. A process for the preparation of a substantially purified TTO 20 polypeptide comprising the amino acid sequence of SEQ ID NO:10, comprising the steps of:

(a) culturing a host cell claimed in claim 5 under conditions that result in the expression of said TTO 20 polypeptide; and (b) isolation of said TTO 20 polypeptide from said host cell or culture medium.

7. A diagnostic kit for the diagnosis of rheumatoid arthritis comprising a polynucleotide as claimed in claim 1.

8. A diagnostic kit for the diagnosis of rheumatoid arthritis comprising a polynucleotide as claimed in claim 2.

9. A diagnostic kit for the diagnosis of rheumatoid arthritis comprising a polynucleotide comprising a sequence that is degenerate to the nucleotide sequence of SEQ ID NO:9.

* * * * *